United States Patent

Desai et al.

[11] Patent Number: 5,240,943
[45] Date of Patent: Aug. 31, 1993

[54] BENZOPYRAN CLASS III ANTIARRHYTHMIC AGENTS

[75] Inventors: Bipinchandra N. Desai, Vernon Hills; Konrad F. Koehler, Glenview; Mark A. Russell, Gurnee, all of Ill.

[73] Assignee: G. D. Searle & Co., Chicago, Ill.

[21] Appl. No.: 810,582

[22] Filed: Dec. 19, 1991

[51] Int. Cl.$^5$ ............... C07D 405/06; A61K 31/445; A61K 31/35
[52] U.S. Cl. ..................................... 514/320; 546/196
[58] Field of Search ................... 514/320; 546/196

[56] References Cited

U.S. PATENT DOCUMENTS 5,025,013  6/1991  Barreau et al. ..................... 514/320

FOREIGN PATENT DOCUMENTS 0379441  7/1990  France .

Primary Examiner—C. Warren Ivy
Assistant Examiner—Phyllis G. Spivack
Attorney, Agent, or Firm—Cynthia S. Kovacevic; Paul D. Matukaitis; Roger A. Williams

[57] ABSTRACT

The present invention relates to compounds of the formula

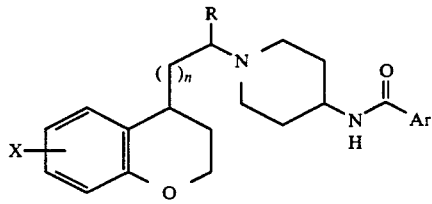

or a pharmaceutically acceptable salt thereof;
wherein n is 0, 1 or 2;
wherein R is H or lower alkyl of 1 to 6 carbon atoms;
wherein X is selected from the group consisting of hydrogen, methane sulfonamide, nitro, cyano, imidazolyl, alkoxy of 1 to 6 carbon atoms and hydroxy; and
wherein Ar is selected from the group consisting of pyridinyl, tetrahydronaphthalenyl, benzofuranyl, and Ph—CH=CH— and phenyl all optionally substituted by methane sulfonamide, nitro, cyano, or imidazolyl with the proviso that when n is 1, Ar is other then phenyl;
pharmaceutical compositions containing these compounds and a method for treating cardiac arrhythmias in mammals by administering the compositions.

17 Claims, No Drawings

BENZOPYRAN CLASS III ANTIARRHYTHMIC AGENTS

BACKGROUND OF THE INVENTION

The present invention relates to pharmaceutical compounds, compositions and methods of their use. Such compounds are pharmacologically useful in the treatment of cardiac arrhythmias in mammals. More specifically, the compounds of the present invention are orally active Class III antiarrhythmic agents which, by effectively prolonging repolarization of a cardiac cell action potential, can be used effectively to treat certain cardiac arrhythmias. At the present time, there is a need in the area of cardiology therapy for such an agent.

Antiarrhythmic drugs have been grouped together according to the pattern of electrophysiological effects that they produce and/or their presumed mechanisms of action. Thus, Class I antiarrhythmic agents are characterized by being sodium channel blockers, Class II antiarrhythmic agents are beta-adrenergic receptor blockers, Class III antiarrhythmic agents prolong repolarization and Class IV antiarrhythmic agents are calcium channel blockers.

Currently, there are very few Class III antiarrhythmic agents available for therapeutic use. Among the available agents is bretylium. Bretylium's usefulness is limited however, and currently its therapeutic use is reserved for life-threatening ventricular arrhythmias that are refractory to therapy. Thus, bretylium's use is generally confined to intensive care units. Sotalol is another known compound being developed as a Class III antiarrhythmic.

Accordingly, it is an object of this invention to provide Class III antiarrhythmic pharmaceutical agents of broader therapeutic use than existing Class III antiarrhythmic agents. There is a need in the area of cardiovascular therapeutics for an agent which has broader clinical usefulness. Various compounds have been disclosed as being useful Class III antiarrhythmics. See for example EP 379,441 and EP 379,440. The compounds of the present invention meet the need for an agent which has broad clinical usefulness by providing for orally active therapeutic agents for the treatment of cardiac arrhythmias.

SUMMARY OF THE INVENTION

The present invention relates to a class of compounds represented by the formula

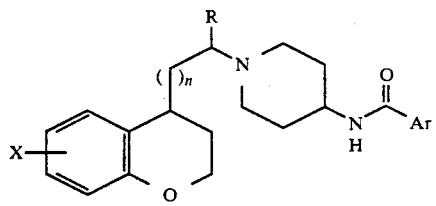

or a pharmaceutically acceptable salt thereof;
wherein n is 0, 1 or 2;
wherein R is H or lower alkyl of 1 to 6 carbon atoms;
wherein X is selected from the group consisting of hydrogen, methane sulfonamide, nitro, cyano, imidazolyl, alkoxy of 1 to 6 carbon atoms and hydroxy; and
wherein Ar is selected from the group consisting of pyridinyl, tetrahydronaphthalenyl, benzofuranyl, Ph—CH=CH— and phenyl all optionally substituted by methane sulfonamide, nitro, cyano or imidazolyl with the proviso that when n is 1, Ar is other then phenyl.

The present invention also provides pharmaceutical compositions useful in treating cardiac arrhythmias comprised of a therapeutically effective amount of the compounds of Formula I in combination with a pharmaceutically acceptable carrier. The present invention further provides a method of treating cardiac arrhythmias in a mammal in need of such treatment.

DETAILED DESCRIPTION OF THE INVENTION

This invention encompasses compounds of the Formula I as previously described.

Within the class of compounds defined by Formula I, there is a sub-class of preferred compounds represented by Formulas II:

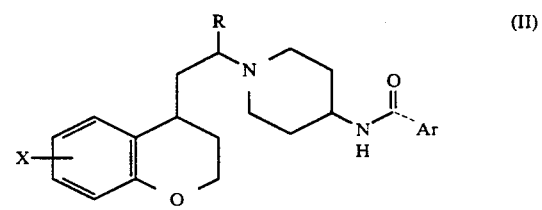

Included in this sub-class are:
N-[1-[2-(3,4-dihydro-2H-1-benzopyran-4-yl)ethyl]-4-piperidinyl]-4-pyridinecarboxamide;
N-[1-[2-(3,4-dihydro-2H-1-benzopyran-4-yl)ethyl]-4-piperidinyl]-3-pyridinecarboxamide;
N-[1-[2-(3,4-dihydro-2H-1-benzopyran-4-yl)ethyl]-4-piperidinyl]-1,2,3,4-tetrahydro-2-naphthalenecarboxamide;
N-[1-[2-(3,4-dihydro-2H-1-benzopyran-4-yl)ethyl]-4-piperidinyl]-2-benzofurancarboxamide;
N-[1-[2-(3,4-dihydro-2H-1-benzopyran-4-yl)ethyl]-4-piperidinyl]-3-phenyl-2E-propenamide.

Another preferred subclass is represented by the formula III:

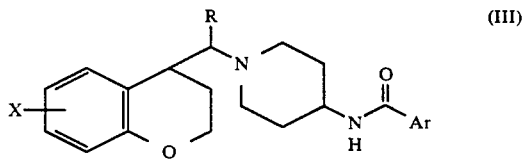

Included within this subclass are the following compounds:
N-[1-[2-(3,4-dihydro-2H-1-benzopyran-4-yl)methyl]-4-piperidinyl]-4-pyridinecarboxamide;
N-[1-[2-(3,4-dihydro-2H-1-benzopyran-4-yl)methyl]-4-piperidinyl]-3-pyridinecarboxamide;
N-[1-[2-(3,4-dihydro-2H-1-benzopyran-4-yl)methyl]-4-piperidinyl]benzenecarboxamide; and
N-[1-[2-(3,4-dihydro-2H-1-benzopyran-4-yl)methyl]-4-piperidinyl]-2-benzofurancarboxamide.

The group X as defined above consists of groups commonly substituted on Class III antiarrhythmics and can be prepared by methodology known in the art. See EP 379,441 and U.S. Pat. No. 4,994,470.

Included within the classes and subclasses of compounds embraced by Formulas I–III are isomeric forms of the described compounds. Pharmaceutically acceptable salts of such compounds are also included as well as pharmaceutically acceptable salts of such isomers.

In the structures herein a bond drawn across a bond in a ring indicates that the bond can be to any available atom of the ring structure.

The term "pharmaceutically acceptable salt," as used herein, refers to conventionally accepted pharmaceutical salts prepared by processes which are well known to those of ordinary skill in the art. (See for example, S. M. Berge, et al., "Pharmaceutical Salts," *J. Pharm. Sci.*, 66:1-19 (1977)).

The term "composition" as used herein means a product which results from the mixing or combining of more than one element or ingredient.

The term "pharmaceutically acceptable carrier" as used herein means a pharmaceutically-acceptable material, composition or vehicle, such as a liquid or solid filler, diluent, excipient, solvent or encapsulating material, involved in carrying or transporting a chemical agent from one organ or portion of the body to another organ or portion of the body.

The term "therapeutically effective amount" shall mean that amount of drug or pharmaceutical agent that will elicit the biological or medical response of a tissue, system or animal that is being sought by a researcher or clinician.

The term "cardiac arrhythmia" is defined to mean any variation from the normal rhythm of the heartbeat, including, without limitation, sinus arrhythmia, premature heartbeat, heartblock, fibrillation, flutter, pulsus alternons, tachycardia, paroxysmal tachycardia and premature ventricular contractions.

The term "repolarization of cardiac cells" is defined as those phases of a cardiac action potential during which time a depolarized cardiac cell is reverting to normal pre-polarization transmembrane voltage.

By virtue of their biological activity the compounds of Formula I are useful in treating cardiac arrhythmias in mammals. A physician or veterinarian of ordinary skill can readily determine whether a subject exhibits such a condition.

This invention also relates to a method of treating cardiac arrhythmias and more specifically, a method of treatment involving the administration of compounds of Formulae I-III.

The compounds of the present invention can be administered in such oral dosage forms as tablets, capsules, softgels pills, powders, granules, elixirs or syrups.

The compounds can also be administered intravascularly, intraperitoneally, subcutaneously, intramuscularly, or topically using forms known in the pharmaceutical art. Moreover, they can be administered rectally or vaginally, in such forms as suppositories or bougies. In general, the preferred form of administration is oral. For the orally administered pharmaceutical compositions and methods of the present invention, the foregoing active ingredients will typically be administered in admixture with suitable pharmaceutical diluents, excipients, or carriers (collectively referred to herein as "carrier" materials) suitably selected with respect to the intended form of administration, that is, oral tablets, capsules, softgels, elixirs, syrups, drops, and the like, and consistent with conventional pharmaceutical practices.

For example, for oral administration in the form of tablets or capsules, a therapeutically effective amount of one or more compounds of the present invention can be combined with any oral pharmaceutically acceptable inert carrier such as lactose, starch, sucrose, cellulose, magnesium stearate, dicalcium phosphate, calcium sulfate, mannitol, and the like, or various combinations thereof. For oral administration in liquid forms, such as in softgels, elixirs, syrups, drops and the like, a therapeutically effective amount of the active drug components can be combined with any oral pharmaceutically acceptable inert carrier such as water, saline, ethanol, polyethylene glycol, propylene glycol, corn oil, cottonseed oil, peanut oil, sesame oil, benzyl alcohol, various buffers, and the like, or various combinations thereof. Moreover, when desired or necessary, suitable binders, lubricants, disintegrating agents, and coloring agents can also be incorporated in the mixture. Suitable binders include starch, gelatin, natural sugars, corn sweeteners, natural and synthetic gums such as acacia, sodium alginate, carboxymethylcellulose, polyethylene glycol, and waxes, or combinations thereof. Lubricants for use in these dosage forms include boric acid, sodium benzoate, sodium acetate, sodium chloride, and the like, or combinations thereof. Disintegrators include, without limitation, starch, methylcellulose, agar, bentonite, guar gum, and the like, or combinations thereof. Sweetening and flavoring agents and preservatives can also be included where appropriate.

For intravascular, intraperitoneal, subcutaneous, or intramuscular administration, one or more compounds of the present invention can be combined with a suitable carrier such as water, saline, aqueous dextrose, and the like. For topical administration, therapeutically effective amounts of one or more compounds of the present invention can be combined with pharmaceutically acceptable creams, oils, waxes, gels and the like.

Regardless of the route of administration selected, the compounds of the present invention are formulated into pharmaceutically acceptable dosage forms by conventional methods known to those skilled in the art. The compounds can also be formulated using pharmacologically acceptable base addition salts. Moreover, the compounds or their salts may be used in a suitable hydrated form.

Regardless of the route of administration selected, a non-toxic but therapeutically effective quantity of one or more compounds of this invention is employed in treatment. The dosage regimen for preventing or treating cardiac arrhythmias with the compounds of this invention is selected in accordance with a variety of factors, including the type, age, weight, sex, and medical condition of the patient, the route of administration, and the particular compound employed in the treatment. A physician or veterinarian of ordinary skill can readily determine and prescribe the effective amount of the drug required to prevent or arrest the progress of the condition. Daily dosages of the compounds of the invention are ordinarily in the range of about 0.1 to about 1000 mg, more preferably in the range of about 1 to about 100 mg.

The compounds of this invention of Formula II are generally prepared according to the reaction Scheme I. The compounds of this invention of Formula III are generally prepared according to the reaction Scheme II. Compounds of the Formula I wherein $n=2$ are generally prepared according to reaction Scheme III which is a variation of Scheme I.

Scheme I
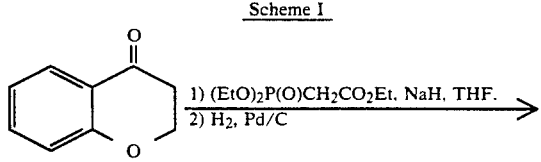
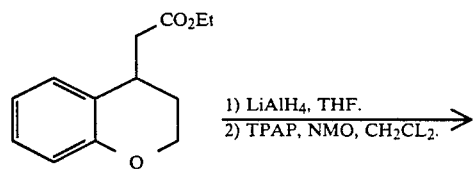
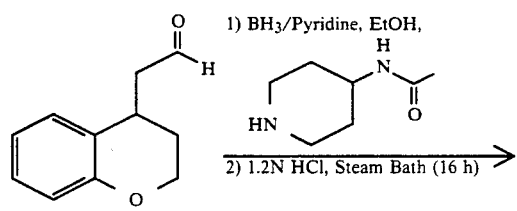
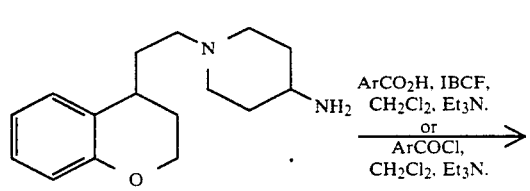
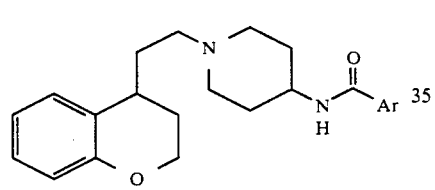
Scheme III
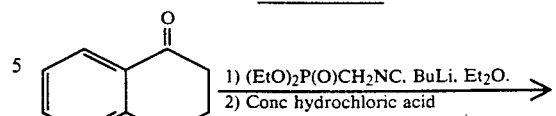
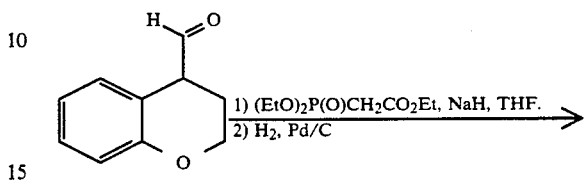
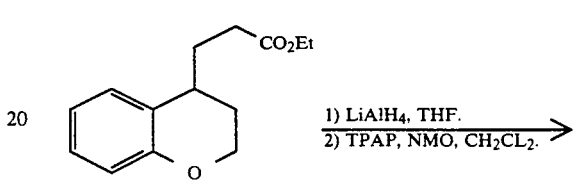
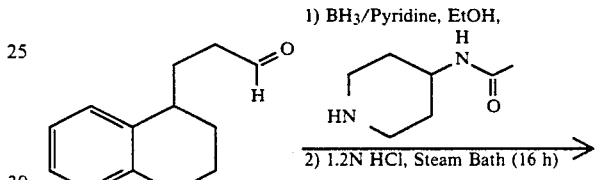
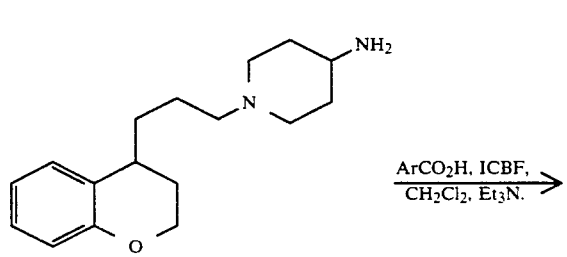
Scheme II
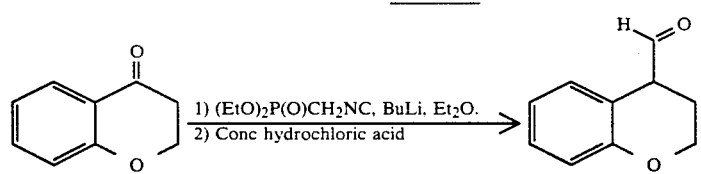
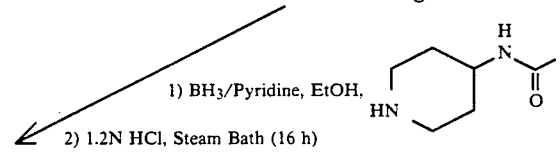
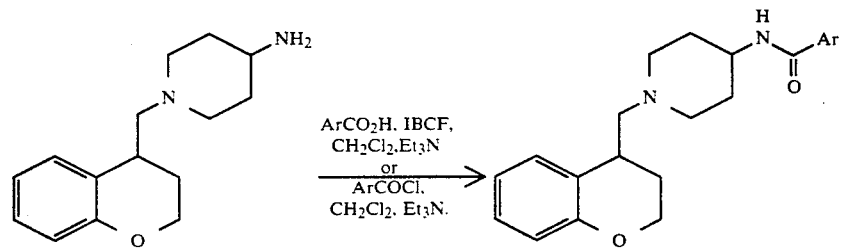

-continued
Scheme III

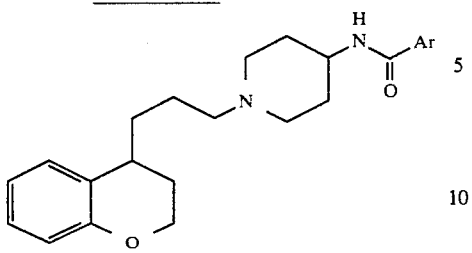

The following examples illustrate the methods used to prepare the compounds of this invention. These examples are given by way of illustration only and are not meant to be construed as limiting the invention in spirit or in scope, as many modifications in materials and methods will be apparent from this disclosure to one having ordinary skill in the art.

EXAMPLE 1

2-(3,4-dihydro-2H-1-benzopyran-4-yl)ethanol was prepared as described in U.S. Pat. No. 4,977,166.

EXAMPLE 2

Preparation of 2-(3,4-dihydro-2H-1-benzopyran-4-yl)ethanal

To a stirred solution of 2-(3,4-dihydro-2H-1-benzopyran-4-yl)ethanol (1.45 g, 8 mmol), N-methylmorpholine-N-oxide (1.41 g, 12 mmol) and 4 A molecular sieves (4.0 g) in methylene chloride (20 ml), tetrapropylammonium perruthenate (0.140 g, 0.4 mmol) was added. The reaction mixture was stirred at room temperature for 15 min., diluted with an equal volume of ethyl acetate (20 ml) and flash filtered through silica gel (eluant: methylene chloride/ethyl acetate 1:1). Concentration of the filtrate in vacuo afforded the title compound as an oily gum (0.92 g, 64%). NMR (300 MHz/CDCl$_3$) 9.87 (1 H, s).

EXAMPLE 3

Preparation of N-[1-[2-(3,4-dihydro-2H-1-benzopyran-4-yl)ethyl]-4-piperidinyl]acetamide To a stirred solution of 2-(3,4-dihydro-2H-1-benzopyran-4-yl]ethanal (2.50 g, 14.28 mmol) and 4-acetamidopiperidine AcOH (2.88 g, 14.28 mmol) (preparation described in U.S. Pat. No. 5,028,616) in ethanol (80 ml) under a nitrogen atmosphere, borane/pyridine complex (1.5 ml, 15 mmol) was added. The reaction mixture was stirred overnight (ca 15 h) and evaporated to an oily gum which was neutralized by careful addition of 10% hydrochloric acid. The acidic solution was extracted with diethyl ether and the diethyl ether extracts were discarded. The acidic aqueous layer was basified by dropwise addition of a 50% sodium hydroxide solution. The basic solution (>pH 12) was extracted with ethyl acetate. The ethyl acetate layer was washed with distilled water, dried (Na$_2$SO$_4$), filtered and evaporated to afford an oily gum (3.56 g). The resulting gum was purified by chromatography on silica (eluant: chloroform/ethanol/ammonium hydroxide; 85/14/1) to afford an oil (2.56 g) which was crystallized from diethyl ether to afford the title compound (2.40 g, 56%) mp=126-8°. Anal: C$_{18}$H$_{26}$N$_2$O$_2$ Calc.: C 71.49; H 8.67; N 9.26; Found C 71.46; H 8.84; N 9.26.

EXAMPLE 4

N-[1-[2-(3,4-dihydro-2H-1-benzopyran-4-yl)ethyl]-4-piperidinyl]2-benzofurancarboxamide

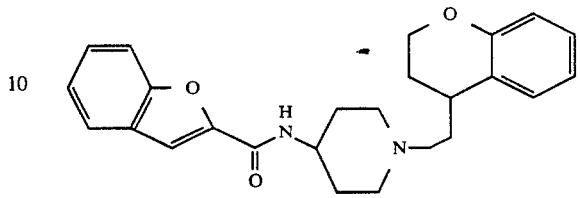

To a stirred solution of 2-(3,4-dihydro-2H-1-benzopyran-4-yl)ethanal (875 mg, 5 mmol) and 4-(2-benzofurancarboxamido) piperidine hydrochloride (1.4 g, 5 mmol) under a nitrogen atmosphere, borane/pyridine complex (0.5 ml, excess) was added. The reaction was stirred overnight (ca 15 h) and evaporated to an oily gum which was neutralized by careful addition of 10% hydrochloric acid. The acidic solution was extracted with diethyl ether. The diethyl ether extracts were discarded. The acidic aqueous layer was basified by dropwise addition of 50% sodium hydroxide. The ethyl acetate layer was washed with distilled water, dried (Na$_2$SO$_4$), filtered and evaporated to afford an oily gum (520 mg). The resulting gum was purified by chromatography on silica (eluant: chloroform/ethanol/ammonium hydroxide; 85/14/1) to afford an oil (260 mg) which was crystallized from diethyl ether to afford the title compound (150 mg, 7%), mp=146-8°. Anal: C$_{25}$H$_{28}$N$_2$O$_3$ 0.5 H$_2$O, Calc. C, 72.62; H, 7.07; N, 6.77; Found C,72.40; H, 6.94; N, 6.83.

EXAMPLE 5

N-[1-[2-(3,4-dihydro-2H-1-benzopyran-4-yl)ethyl]-4-aminopiperidine

A solution of N-[1-[2-(3,4-dihydro-2H-1-benzopyran-4-yl)ethyl]-4-piperidinyl]acetamide (3.3 g, 10.9 mmol) in 1.2N hydrochloric acid (35 ml) was heated on a steam bath for 16 h. The reaction mixture was cooled and neutralized with 50% sodium hydroxide solution (pH 12). The basic aqueous solution was extracted with ethyl acetate. The organic extracts were washed with distilled water, dried (Na$_2$SO$_4$), filtered and evaporated in vacuo to afford the title compound (2.85 g, 100%) as an oily gum.

The title compound was used in the subsequent experiments without purification but could be further purified by the following means: To a solution of the title compound (100 mg) in methanol (0.2 ml), 6N dioxane/HCl (0.5 ml) is added. The resulting solution is evaporated in vacuo to afford a solid residue which is crystallized from methanol/diethyl ether to afford the title compound as its dihydrochloride salt (60 mg), Anal: C$_{16}$H$_{24}$N$_2$O.2HCl.0.25 H$_2$O, Calc, C, 56.89; H, 7.91: N, 8.29; Found C, 56.67; H, 7.87; N, 8.19.

EXAMPLE 6

N-[1-[2-(3,4-dihydro-2H-1-benzopyran-4-yl)ethyl]-4-piperidinyl]1,2,3,4-tetrahydro-2-naphthalene carboxamide

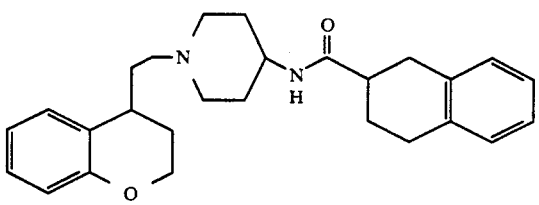

To a stirred solution of 1,2,3,4-tetrahydronaphthalene-2-carboxylic acid (176 mg, 1 mmol) and triethylamine (0.25 ml) in methylene chloride (5 ml), isobutylchloroformate (136 mg, 1 mmol) was added. After 5 minutes N-[1-[2-(3,4-dihydro-2H-1-benzopyran-4-yl)ethyl]-4-aminopiperidine (260 mg, 1 mmol) in methylene chloride was added and the reaction mixture was stirred at room temperature for 16 h. The reaction mixture was quenched with 2N potassium hydroxide solution. The organic layer was separated, washed with distilled water and dried ($Na_2SO_4$). Evaporation of the solvent gave a white solid which was crystallized from diethyl ether to afford the title compound (140 mg, 33%), m.p.=130–2°, Anal $C_{27}H_{34}N_2O_2.0.25$ $H_2O$, Calc, C, 76.65; H, 8.22, N, 6.62; Found C,76.34; H, 8.32; N, 6.59.

EXAMPLE 7

N-[1-[2-(3,4-dihydro-2H-1-benzopyran-4-yl)ethyl]-4-piperidinyl]-3-phenyl-2E-propenamide

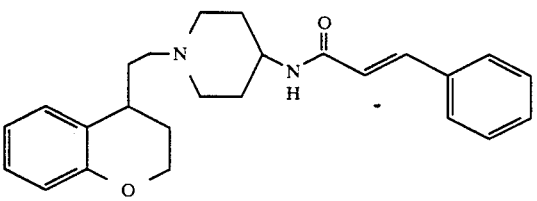

N-[1-[2-(3,4-dihydro-2H-1-benzopyran-4-yl)ethyl]-4-aminopiperidine was coupled to 3-phenyl-2E-propenoic acid utilizing the isobutylchloroformate protocol described in Example 6. This afforded the title compound; (61% yield) m.p. 168–70°, Anal: $C_{25}H_{30}N_2O_2$ 0.3 $H_2O$, Calc. C, 75.84; H, 7.79; N, 7.08; Found, C, 75.90; H, 7.94; N, 7.32.

EXAMPLE 8

N-[1-[2-(3,4-dihydro-2H-1-benzopyran-4-yl)ethyl]-4-piperidinyl]-3-pyridinecarboxamide

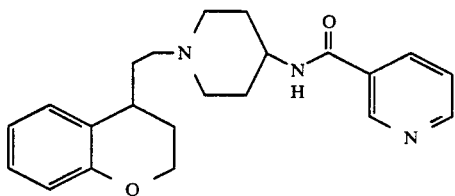

N-[1-[2-(3,4-dihydro-2H-1-benzopyran-4-yl)ethyl]-4-aminopiperidine was coupled to pyridine-3-carboxylic acid utilizing the isobutylchloroformate protocol described in Example 6. The resulting residue was further purified by chromatography on silica (eluant: chloroform/ethanol/ammonium hydroxide; 85/14/1) and crystallization from diethyl ether to afford the title compound (15% yield), mp=126–8°, Anal: $C_{22}H_{27}N_3O_2 0.25$ $H_2O$, Calc. C, 71.42; H, 7.49; N, 11.36; Found: C, 71.25; H, 7.50; N, 11.19.

EXAMPLE 9

N-[1-[2-(3,4-dihydro-2H-1-benzopyran-4-yl)ethyl]-4-piperidinyl]-4-pyridinecarboxamide

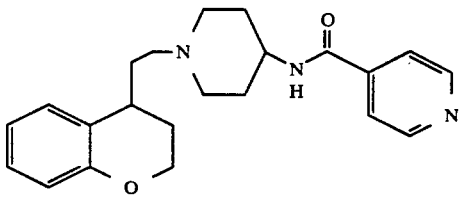

A solution of pyridin-4-oyl chloride (178 mg, 1 mmol) and triethylamine (0.25 ml) in methylene chloride (10 ml), was stirred. After 5 min. N-[1-[2-[(3,4-dihydro-2H-1-benzopyran-4-yl]ethyl]-4-aminopiperidine (260 mg, 1 mmol) in methylene chloride was added and the reaction mixture was stirred at room temperature for 16 h. The reaction mixture was quenched with 2N potassium hydroxide solution. The organic layer was separated, washed with distilled water and dried ($Na_2SO_4$). Evaporation of the solvent gave a white solid which was crystallized from diethyl ether to afford the title compound; (140 mg, 38%), mp=122–3°, Anal: $C_{22}H_{27}N_3O_2.0.25$ $H_2O$, Calc, C, 71.42; H, 7.49; N, 11.36; Found: C, 71.52; H, 7.62; N, 11.20.

EXAMPLE 10

2-(3,4-dihydro-2H-1-benzopyran-4-yl)methanal

To a stirred solution of diethyl(isocyanomethyl)phosphonate (3.6 g, 20 mmol) in anhydrous diethyl ether (75 ml) at −50° nitrogen atmosphere, N-butyllithium (9 ml, 2.5 mol in hexane) was added. The resulting heterogenous mixture was stirred for 15 min. and then chroman-4-one (3.0 g, 20 mmol) in diethyl ether (10 ml) was added. The reaction mixture was then stirred for 2 h at 0°. The reaction mixture was quenched with water followed by concentrated hydrochloric acid (30 ml). The resulting biphasic solution was stirred for a further 12 h, then the organic layer was separated, washed with water, dried ($Na_2SO_4$) and concentrated in vacuo. The resulting oily gum was further purified by chromatography on silica (eluant: diethyl ether/hexane; 1/9) to afford the title compound (1.2 g, 37%). This compound was used as is and fully characterized at the next stage.

EXAMPLE 11

N-[1-[2-(3,4-dihydro-2H-1-benzopyran-4-yl)methyl]-4-piperidinyl]acetamide

To a stirred solution of 2-(3,4-dihydro-2H-1-benzopyran-4-yl)methanal (968 mg, 6 mmol) and 4-acetamidopiperidine AcOH (1.2 g, 6 mmol) preparation described in U.S. Pat. No. 5,028,616) in ethanol (25 ml) under a nitrogen atmosphere, borane/pyridine complex (0.6 ml) was added. The reaction mixture was stirred overnight (ca 15 h) evaporated to an oily gum which was neutralized by careful addition of 10 % hydrochloric acid. The acidic solution was extracted with diethyl ether. The diethyl ether extracts were discarded. The acidic aqueous layer was basified by dropwise addition of 50% sodium hydroxide solution. The basic solution (>pH 12) was extracted with ethyl acetate. The ethyl acetate layer was washed with distilled water, dried ($Na_2SO_4$), filtered and evaporated to afford an oily gum. The resulting gum was crystallized from diethyl ether to afford the title compound (1.1 g, 64%), mp=202-5° C., Anal: $C_{17}H_{24}N_2O_2$, Calc., C, 70.80; H, 8.39, N 9.71; Found C, 70.49; H, 8.35; N, 9.69.

EXAMPLE 12

N-[1-[2-(3,4-dihydro-2H-1-benzopyran-4-yl)methyl]-4-aminopiperidine

A solution of N-[1-[2-(3,4-dihydro-2H-1-benzopyran-4-yl)methyl]-4-piperidinyl]acetamide (950 mg, 3.3 mmol) in 1.2N hydrochloric acid (10 ml) was heated on a steam bath for 16 h. The reaction mixture was cooled and neutralized with a 50% sodium hydroxide solution (pH=12). The basic aqueous solution was extracted with ethyl acetate. The organic extracts were washed with distilled water, dried ($Na_2SO_4$), filtered and evaporated in vacuo to afford the title compound (800 mg, 98%) as an oily gum. The title compound was used in the subsequent experiments without further purification but could be further purified by the following means.

To a solution of the title compound (50 mg) in methanol (0.2 ml) 6N dioxane/HCL (0.5 ml) was added. The resulting solution was evaporated in vacuo to afford a solid residue which crystallized from methanol/diethyl ether to afford the title compound as its dihydrochloride salt (60 mg), Anal: $C_{15}H_{22}N_2O$ 2 HCl 0.75 $H_2O$, Calc., C, 54.19; H, 7.72; N, 8.46; Found, C, 53.89; H, 7.30; N, 8.20.

EXAMPLE 13

N-[1-[2-(3,4-dihydro-2H-1-benzopyran-4-yl)methyl]-4-piperidinyl]-3-pyridinecarboxamide dihydrochloride

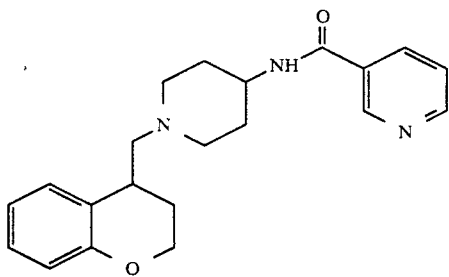

To a stirred solution of pyridin-3-oyl chloride (199 mg, 1.12 mmol) and triethylamine (0.3 ml) in methylene chloride (5 mol), was added. After 5 min. N-[1-[2-(3,4-dihydro-2H-1-benzopyran-4-yl]methyl]-4-aminopiperidine (282 mg, 1.12 mmol) in methylene chloride was added and the reaction mixture was stirred at room temperature for 16 h. The reaction mixture was quenched with 2N potassium hydroxide solution. The organic layer was separated, washed with distilled water and dried ($Na_2SO_4$). Evaporation of the solvent afforded an oily gum which was converted into its dihydrochloride salt on addition of 6N HCl/dioxane. Crystallization from diethyl ether afforded the title compound; (80 mg, 16%), mp>260° C. Anal: $C_{21}H_{25}N_3O_2$ 2 HCl 1 MeOH, Calc: C, 57.90; H, 6.85; N, 9.21; Found, C 58.19; H, 6.61; N, 9.00.

EXAMPLE 14

N-[1-[2-(3,4-dihydro-2H-1-benzopyran-4-yl)methyl]-4-piperidinyl]benzenecarboxamide

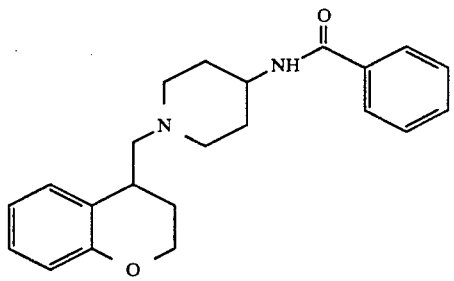

To a stirred solution of benzoyl chloride (102 mg, 0.73 mmol) and triethylamine (0.2 ml) in methylene chloride (5 ml) was added. After 5 min. N-[1-[2-(3,4-dihydro-2H-1-benzopyran-4-yl)methyl]-4-aminopiperidine (180 mg, 0.73 mmol) in methylene chloride was added and the reaction mixture was stirred at room temperature for 16 h. The reaction mixture was quenched with 2N potassium hydroxide solution. The organic lay was separated, washed with distilled water and dried ($Na_2SO_4$). Evaporation of the solvent and crystallization from diethyl ether afforded the title compound as a white solid (181 mg, 67%), mp>260° C., Anal: $C_{22}H_{26}N_2O_2$ $H_2O$, Calc., C, 71.71; H, 7.66; N, 7.60; Found, C, 71.86; H, 7.42; N, 7.69.

EXAMPLE 15

N-[1-2-(3,4-dihydro-2H-1-benzopyran-4-yl)methyl]-4-piperidinyl]-4-pyridinecarboxamide dihydrochloride

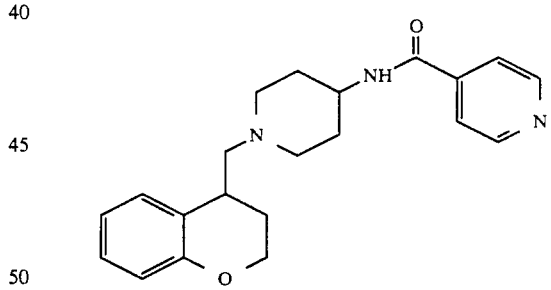

To a stirred solution of benzoyl chloride (102 mg, 0.73 mmol) and triethylamine (0.2 ml) in methylene chloride (5 ml), was added. After 5 min. N-[1-2-(3,4-dihydro-2H-1-benzopyran-4-yl)methyl]-4-aminopiperidine (246 mg, 1.0 mmol) in methylene chloride was added and the reaction mixture was stirred at room temperature for 16 h. The reaction mixture was quenched with 2N potassium hydroxide solution. The organic layer was separated, washed with distilled water and dried ($Na_2SO_4$). Evaporation of the solvent afforded an oily gum which was converted into it dihydrochloride salt on addition of 6N HCl/dioxane. Crystallization from diethyl ether afforded the title compound; (310 mg, 70%), mp>260° C., Anal: $C_{21}H_{25}N_3O_2$ 2 HCl 1 $H_2O$, Calc. C, 57.02; H, 6.61; N, 9.50; Found, C,57.11; H, 6.67; N, 9.25.

EXAMPLE 16

N-[1-[2-(3,4-dihydro-2H-1-benzopyran-4-yl)methyl]-4-piperidinyl]-2-benzofurancarboxamide

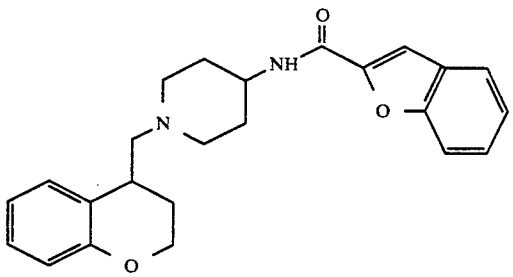

N-[1-[2-(3,4-dihydro-2H-1-benzopyran-4-yl)ethyl]-4-aminopiperidine was coupled to benzofuran-2-carboxylic acid utilizing the isobutylchloroformate protocol described in example 6. This afforded the title compound which was isolated as its hydrochloride salt (26%). Anal: $C_{24}H_{26}N_2O_3$ 1 HCl 0.5 $H_2O$, Calc. C, 66.12; H, 6.47; N, 6.43; Found, C, 66.04; H, 6.83; N, 6.74.

In vitro Experimental

Guinea pigs, of either sex weighing between 200 to 350 g are acutely sacrificed and the right ventricular papillary muscle is isolated. A sample of a given test compound is added using an in vitro tissue bath. Concentrations used are generally $3 \times 10^{-5}$ M, but may also be as low as $3 \times 10^{-7}$ M. Changes in refractory period are measured before and after adding 1 concentration (usually $3 \times 10^{-5}$ M, as noted above) of a test compound to the bath. One hour is allowed for drug equilibration. The activity of a Class III anti-arrhythmic compound is determined by a measurement of ventricular refractory period [at 1 Hz]. The following table shows the results of the assay performed on the compounds herein and in comparison to known class III compounds diisopyramide, clofilium and D-sotalol and also water as a control.

| Compound | Concentration (M) | Change (msec) |
| --- | --- | --- |
| $H_2O$ | 0 | 8 |
| Disopyramide | $3 \times 10^{-5}$ | 20 |
| Clofilium | $3 \times 10^{-5}$ | 24 |
| D-Sotalol | $3 \times 10^{-5}$ | 40 |
| Example 9 | $3 \times 10^{-6}$ | 70 |
| Example 8 | $3 \times 10^{-6}$ | 60 |
| Example 6 | $1 \times 10^{-6}$ | 35 |
| Example 4 | $3 \times 10^{-7}$ | 45 |
| Example 7 | $1 \times 10^{-6}$ | 45 |
| Example 14 | $3 \times 10^{-6}$ | 35 |
| Example 15 | $3 \times 10^{-6}$ | 125 |

What is claimed is:

1. A compound of the formula

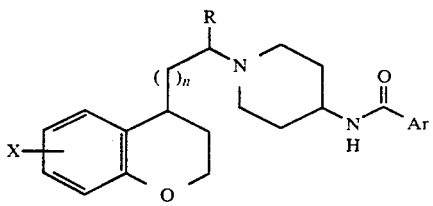

or a pharmaceutically acceptable salt;

wherein n is 0, 1 or 2;
wherein R is H or lower alkyl of 1 to 6 atoms;
wherein X is selected from the group consisting of hydrogen, methane sulfonamide, nitro, cyano, alkoxy of 1 to 6 carbon atoms and hydroxy; and
wherein Ar is selected from the group consisting of tetrahydronaphthalenyl, Ph—CH=CH— and phenyl all optionally substituted by methane sulfonamide, nitro, cyano or imidazolyl, with the proviso that when n is 1, Ar is other than phenyl.

2. A compound according to claim 1 wherein n is 1.
3. A compound according to claim 2 wherein Ar is tetrahydronaphthalenyl.
4. A compound according to claim 3 which is N-[1-[2-(3,4-dihydro-2H-1-benzopyran-4-yl)ethyl]-4-piperidinyl]-1,2,3,4-tetrahydro-2-naphthalenecarboxamide.
5. A compound according to claim 2 wherein Ar is Ph—CH=CH—.
6. A compound according to claim 5 which is N-[1-[2-(3,4-dihydro-2H-1-benzopyran-4-yl)ethyl]-4-piperidinyl]-3-phenyl-2E-propenamide.
7. A compound according to claim 1 wherein n is 0.
8. A compound according to claim 7 wherein Ar is phenyl.
9. A compound according to claim 8 which is N-[1-[2-(3,4-dihydro-2H-1-benzopyran-4-yl)methyl]-4-piperidinyl]benzenecarboxamide.
10. A pharmaceutical composition comprising a therapeutically effective amount of a compound of the formula or a pharmaceutically acceptable salt thereof;
wherein n is 0, 1 or 2;
wherein R is H or lower alkyl of 1 to 6 carbon atoms;
wherein X is selected from the group consisting of hydrogen, methane sulfonamide, nitro, cyano, alkoxy of 1 to 6 carbon atoms and hydroxy; and
wherein Ar is selected from the group consisting of tetrahydronaphthalenyl, Ph—CH=CH— and phenyl all optionally substituted by methane sulfonamide, nitro, cyano or imidazolyl with the proviso that when n is 1, Ar is other than phenyl; and
a pharmaceutically acceptable carrier.

11. A pharmaceutical composition according to claim 10 wherein the compound is N-[1-[2-(3,4-dihydro-2H-1-benzopyran-4-yl)ethyl]-4-piperidinyl]-1,2,3,4-tetrahydro-2-naphthalenecarboxamide.
12. A pharmaceutical composition according to claim 10 wherein the compound is N-[1-[2-(3,4-dihydro-2H-1-benzopyran-4-yl)ethyl]-4-piperidinyl]-3-phenyl-2E-propenamide.
13. A pharmaceutical composition according to claim 10 wherein the compound is N-[1-[2-(3,4-dihydro-2H-1-benzopyran-4-yl)methyl]-4-piperidinyl]benzenecarboxamide.
14. A method of treating cardiac arrhythmias in mammals comprising administering to a patient in need of such treatment, a therapeutically effective amount of a compound of the formula

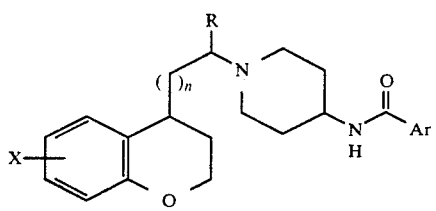

or a pharmaceutically acceptable salt thereof;
wherein n is 0, 1 or 2;
wherein R is H or lower alkyl of 1 to 6 carbon atoms;
wherein X is selected from the group consisting of hydrogen, methane sulfonamide, nitro, cyano, alkoxy of 1 to 6 carbon atoms and hydroxy; and
wherein Ar is selected from the group consisting of tetrahydronaphthalenyl, Ph—CH=CH— and phenyl all optionally substituted by methane sulfonamide, nitro, cyano or imidazolyl, with the proviso that when n is 1, Ar is other than phenyl.

15. A method of treating cardiac arrhythmias in mammals according to claim 14 wherein the compound is N-[1-[2-(3,4-dihydro-2H-1-benzopyran-4-yl)ethyl]-4-piperidinyl]-1,2,3,4-tetrahydro-2-naphthalenecarboxamide.

16. A method of treating cardiac arrhythmias in mammals according to claim 14 wherein the compound is N-[1-[2-(3,4-dihydro-2H-1-benzopyran-4-yl)ethyl]-4-piperidinyl]-3-phenyl-2E-propenamide.

17. A method according to claim 14 wherein the compound is N-[1-[2-(3,4-dihydro-2H-1-benzopyran-4-yl)methyl]-4-piperidinyl]benzenecarboxamide.

* * * * *